US012689201B2

(12) United States Patent
Gross et al.

(10) Patent No.: US 12,689,201 B2
(45) Date of Patent: Jul. 21, 2026

(54) CABLE GUIDE FOR A COMPUTED TOMOGRAPHY SYSTEM

(71) Applicant: Siemens Healthineers AG, Forccheim (DE)

(72) Inventors: Stefan Gross, Trabitz (DE); Matthias Hupfauf, Nabburg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 284 days.

(21) Appl. No.: 18/359,092

(22) Filed: Jul. 26, 2023

(65) Prior Publication Data

US 2024/0039266 A1      Feb. 1, 2024

(30) Foreign Application Priority Data

Jul. 29, 2022      (EP) ..................................... 22187855
Mar. 23, 2023      (EP) ..................................... 23163770

(51) Int. Cl.
H02G 11/00          (2006.01)
A61B 6/00          (2024.01)
          (Continued)

(52) U.S. Cl.
CPC ............. H02G 11/00 (2013.01); A61B 6/032 (2013.01); A61B 6/035 (2013.01); A61B 6/4405 (2013.01);
          (Continued)

(58) Field of Classification Search
CPC ....... A61B 6/4435; A61B 6/56; A61B 6/4464; A61B 6/035; A61B 6/4405; A61B 6/032; A61B 6/447; A61B 6/10; A61B 6/06; A61B 6/4411; A61B 6/4447; A61B 6/4014; A61B 6/4441; A61B 6/4007; A61B 6/504;
          (Continued)

(56) References Cited

U.S. PATENT DOCUMENTS 2,997,585 A      8/1961      Schiring
4,879,737 A      11/1989      Grady
          (Continued)

FOREIGN PATENT DOCUMENTS

CN          113086758 A      7/2021
CN          215710737 U      2/2022
          (Continued)

*Primary Examiner* — Irakli Kiknadze
(74) *Attorney, Agent, or Firm* — Harness, Dickey & Pierce, P.L.C.

(57)          ABSTRACT

A cable guidance system for a computed tomography system, wherein a gantry of the computed tomography system is repositionable in a direction of movement perpendicular to the gantry, the cable guidance system comprising: a vertical column arranged on the gantry and running vertically upward from a base of the computed tomography system; and a first articulated arm and a second articulated arm. The first articulated arm is rotatably connected to an upper end of the vertical column above the gantry via a first point of articulation, and rotatably connected, via a second point of articulation, to the second articulated arm which is likewise arranged above the gantry. At least one supply line runs in a repositionably guided manner along longitudinal axes of the first and second articulated arms.

23 Claims, 5 Drawing Sheets

(51) Int. Cl.
    *A61B 6/03*          (2006.01)
    *H02G 3/04*        (2006.01)

(52) U.S. Cl.
    CPC .......... *A61B 6/4435* (2013.01); *A61B 6/4464*
         (2013.01); *A61B 6/56* (2013.01); *H02G*
         *3/0456* (2013.01)

(58) Field of Classification Search
    CPC ... A61B 6/4085; A61B 6/4452; A61B 6/4458;
        A61B 6/0407; A61B 5/055; A61B 6/508;
              A61B 6/586; A61B 34/30; A61B
           2090/3764; A61B 90/36; A61B 90/50;
        A61B 6/4233; A61B 6/467; A61B 6/027;
          A61B 6/00; A61B 6/04; A61B 6/42;
        A61B 6/40; H02G 3/0456; H02G 11/00;
        H05G 1/10; H05G 1/02; G01R 33/381;
         B25J 15/0019; B25J 19/0025; B25J
                         19/0029
    USPC ........................................................ 378/194
    See application file for complete search history.

(56)            References Cited

U.S. PATENT DOCUMENTS

| | | |
|---|---|---|
| 5,327,474 A | 7/1994 | Inoue et al. |
| 5,410,767 A | 5/1995 | Barud |
| 5,448,607 A | 9/1995 | McKenna |
| 5,490,652 A | 2/1996 | Martin |
| 5,521,957 A | 5/1996 | Hansen |
| 5,901,200 A | 5/1999 | Krause |
| 6,431,751 B1 | 8/2002 | Everett et al. |
| 7,018,097 B2 | 3/2006 | Schmitt |
| 8,967,573 B2* | 3/2015 | Hemmer ................. F16G 13/16 |
| | | 248/323 |
| 9,523,463 B2 | 12/2016 | Abri et al. |
| 11,279,246 B2 | 3/2022 | Shin |
| 11,963,809 B2 | 4/2024 | Van Pinxteren et al. |
| 2009/0154652 A1* | 6/2009 | Yi ......................... A61B 6/4464 |
| | | 378/194 |
| 2017/0360387 A1 | 12/2017 | Gregerson et al. |
| 2018/0312377 A1* | 11/2018 | Jakober ..................... F16F 1/12 |
| 2019/0090830 A1 | 3/2019 | Gao |
| 2021/0308878 A1* | 10/2021 | Yoo ...................... H02G 3/0456 |
| 2023/0355194 A1* | 11/2023 | Gregerson ............. A61B 6/035 |
| 2024/0032883 A1 | 2/2024 | Gross |
| 2024/0039266 A1 | 2/2024 | Gross et al. |

FOREIGN PATENT DOCUMENTS

| | | |
|---|---|---|
| DE | 102008035196 A1 | 2/2010 |
| DE | 102018219541 A1 | 5/2020 |
| DE | 102021202983 A1 | 4/2022 |
| JP | H09220223 A | 8/1997 |

\* cited by examiner

CABLE GUIDE FOR A COMPUTED TOMOGRAPHY SYSTEM

CROSS-REFERENCE TO RELATED APPLICATION(S)

The present application claims priority under 35 U.S.C. § 119 to European Patent Application No. 22187855.6, filed Jul. 29, 2022, and to European Patent Application No. 23163770.3, filed Mar. 23, 2023, the entire contents of each of which are incorporated herein by reference.

FIELD

One or more example embodiments of the present invention provide a cable guidance system for a mobile computed tomography system, which is at least in part ceiling-mounted or extends above the gantry of the computed tomography system. One or more example embodiments of the present invention also provide computed tomography system having such a cable guidance system.

BACKGROUND

Regardless of the gendered pronouns used for a given term, these are intended to include persons identifying as male, female or another gender identity.

Modern medical examination and treatment facilities are making increasing use of mobile computed tomography (CT) systems. The primary purpose of system mobility is to reposition typically large and bulky CT systems in order to provide space in the immediate vicinity of the patient for medical personnel and/or other systems or equipment which are used during an examination, treatment and/or intervention. The emphasis here is on the wellbeing and safety not only of the patient but also of the operating personnel and the machines.

In addition, mobility of the CT systems also opens up the possibility of being able to use them in various treatment rooms and accordingly reduce capital and maintenance costs in the long term.

It is known to reposition CT systems along rails such that the CT systems can adopt predefined positions along the rails. Alternatively, freely mobile CT systems are also commercially available. While freely mobile CT systems have a rechargeable on-board energy supply, for example in the form of a lithium ion battery, the challenge arises for rail-guided systems of providing a wired supply.

In CT systems which are used in different, typically two, treatment rooms, cable guidance systems must be mobile and flexible, specifically such that they can bridge distances of up to 12 m. The applied mechanical loads must not, however, impair the service life of the cable guidance system.

It must additionally be ensured that the cable guidance system itself cannot cause any collisions with the patient, medical personnel or surrounding equipment during a repositioning movement of the CT system.

SUMMARY

The prior art accordingly provides solutions for cable guides which are arranged in the floor, typically in the vicinity of the rail system where collisions are largely ruled out. However, these solutions place structural requirements on the hospital environment and are therefore not universally usable. In addition, they are often not adapted to the hygiene requirements of a medical environment and are costly.

Solutions are alternatively known in which supply lines are arranged in a ceiling box by way of one or more energy guide chains. The rail system here runs parallel to the longitudinal axis of the ceiling box. On the gantry, a vertical column moved together therewith is provided through which the supply lines are guided down to the foot of the gantry and connected there. The length of the ceiling box here defines the maximum repositioning path for the gantry.

It is accordingly an object of embodiments of the present invention to provide alternative mechanisms and/or means for a cable guide for a mobile CT system, which combine an extended service life and low construction costs with greater movement flexibility. In particular, it is an object of embodiments of the present invention to increase the freedom of movement of cable- and rail-guided CT systems to such an extent that they can be used in different treatment rooms with an opposing operating direction. It is furthermore an object of embodiments of the present invention to further reduce the footprint of a mobile computed tomography system.

At least said object is achieved by a cable guidance system for a computed tomography system as claimed in the independent claim(s) and a computed tomography system comprising the cable guidance system as claimed in an independent claim.

The cable guidance system according to a first aspect of embodiments of the present invention serves to supply a computed tomography system, in particular with energy. A supply line is accordingly an electrical cable. Alternatively or additionally, the supply line serves for data communication from or to the computed tomography system. Data is in the form, for example, of raw data or already reconstructed image data. Data may also comprise control data relating to operation of the computed tomography system. In this respect the supply line may also or alternatively take the form of a data cable. The cable guidance system is configured to guide or receive one or more supply lines. In some embodiments, a supply line may comprise up to 40 cables or lines. The gantry of the computed tomography system is configured as repositionable, specifically in a direction of movement running perpendicular to the gantry. The gantry has a central opening, the bore, in which a patient can at least in part be positioned for imaging. According to embodiments of the present invention, the longitudinal axis of the patient corresponds to the direction of movement of the gantry.

In this respect, the patient is hereinafter assumed, without limiting general applicability, to be a person. In principle, the patient may also be an animal.

According to the first aspect of the present invention, the cable guidance system comprises a vertical column which is arranged on the gantry and runs vertically upward from a base of the computed tomography system. The vertical column ends at the floor end on or with the base of the gantry and is consequently moved together with the gantry when the latter is displaced the direction of movement. The vertical column has a height which is greater than the height of the gantry including the base. The vertical column thus exceeds the gantry in height. The vertical column is also dimensioned such that it can receive or guide in itself at least one supply line, preferably a plurality of supply lines. In some embodiments, the vertical column consists of an aluminum sheet or of a plastics material.

The cable guidance system further comprises a first articulated arm and a second articulated arm. The first articulated arm is rotatably connected above the gantry via a first point of articulation to the upper, i.e. ceiling-oriented, end of the vertical column. In other words, the first articulated arm can modify its relative position to the gantry by rotating or by pivoting about the first point of articulation. The first articulated arm is further rotatably connected via a second point of articulation to the second articulated arm which is likewise arranged above the gantry. In other words, the first articulated arm can modify its relative position to the second articulated arm by rotating or by pivoting about the second point of articulation.

Both the vertical column and the first and second articulated arms are configured to guide at least one supply line, preferably a plurality of supply lines, which are then parallel to one another or arranged adjacent one another, at least in part in each case along their longitudinal axes. As already explained above with regard to the vertical column, the individual components of the cable guidance system in each case form cavities or internal regions at least partially shielded from the outside which in each case extend in the longitudinal direction of the components and in or on which the at least one supply line can be received, arranged or integrated. Due to the first and second points of articulation and the first articulated arm, the movement of the gantry of the CT system is decoupled from the second articulated arm, so ensuring greater flexibility with regard to the positionability of the gantry.

Specifically, the at least one supply line runs in a repositionably guided manner along the longitudinal axes of the first and second articulated arms. This means that, on the one hand, the supply line is guided or runs parallel or substantially parallel to the longitudinal axes of the articulated arms and the vertical column. On the other hand, it means that the supply line can be repositioned or displaced along its longitudinal axis relative to the articulated arms. In other words, the relative position of the supply line to the two articulated arms can be modified. In particular, in some embodiments of the present invention, the supply line is configured to slide along the articulated arms. With regard to the vertical column, the relative position of the supply line is preferably fixed or unmodifiable.

In some embodiments of the present invention, the two articulated arms are produced from sheet steel, the production process in particular comprising laser processing and bending. Production need not, however, be limited to these two steps. The articulated arms are thus comparatively inexpensive to produce and low in weight, which reduces the requirements placed on the design of the drive units.

In one preferred embodiment of the cable guidance system according to the present invention, a first and/or a second deflection roller, about which the supply line runs in a circumferentially repositionably guided manner, is/are provided on the first and/or second articulated arm(s). Preferably, more than one deflection roller is provided. According to embodiments of the present invention, the supply line extends circumferentially on or about a circumferential surface of the deflection roller. The at least one deflection roller is preferably arranged at one of the points of articulation. The deflection roller is rotatable about its axis of rotation, which extends parallel to its circumferential surface. If the cable guidance system is repositioned due to a repositioning movement of the gantry of the computed tomography system, the supply line is displaced lengthwise along the articulated arms. Because the supply line is resting against the deflection roller, the latter is rotated by the movement of the supply line and so ensures low-friction deflection of the supply line. The inventors have recognized that, with the assistance of the at least one deflection roller in at least one of the points of articulation, it is advantageously possible to avoid reserve loops at the points of articulation without having to limit the mobility of the cable guidance system.

In one embodiment of the present invention, a cylinder segment, about which the supply line runs in a circumferentially repositionably guided manner, is arranged in the first point of articulation. In a preferred embodiment, the cylinder segment has a substantially semicircular base area. In one particularly preferred embodiment, the base area is even configured somewhat larger than a semicircle. In one embodiment of the present invention, the cylinder segment is fastened with its planar cross-sectional area to the vertical column, in particular adjacent or near to a connection or fastening point for the supply line likewise provided on the vertical column. Up to this point, the relative position between the supply line and vertical column is fixed. The arrangement according to embodiments of the present invention of the cylinder segment ensures that, as a function of the position between the vertical column and first articulated arm, the supply line at least in part runs circumferentially on the circumferential surface of the cylinder segment or rests thereagainst. Depending on the relative position between first articulated arm and gantry, the supply line thus to a greater or lesser extent rests against the circumferential surface of the cylinder segment. The cylinder segment advantageously causes the supply line to be guided directly behind the connection point.

In connection with the cylinder segment, repositionable guidance does not mean lengthwise displacement of the supply line relative to the cylinder segment, but instead the supply line being laid against or removed from the circumferential surface of the cylinder segment. In other words, the path over which the supply line rests circumferentially against the cylinder segment varies depending on the relative position between vertical column and first articulated arm.

According to one particularly preferred configuration of the cable guidance system according to embodiments of the present invention, the first deflection roller is arranged at the second point of articulation. In other words, in this embodiment, the first deflection roller ensures optimum deflection of the supply line between the first and second articulated arms for a plurality of relative positions between the first and second articulated arms, i.e. for a plurality of angular positions between the two articulated arms, and does so without a reserve loop being necessary at the second point of articulation.

In a preferred embodiment of the cable guidance system, the second articulated arm is further rotatably connected above the gantry via a ceiling-mounted third point of articulation. The third point of articulation is consequently arranged close to or on a ceiling of an examination or treatment environment. In some embodiments, the third point of articulation may be stationarily positioned on the ceiling. In alternative embodiments, the position of the third point of articulation is also configured as repositionable, preferably in a direction parallel to the direction of movement of the gantry, as is explained in greater detail below.

The second articulated arm is thus indirectly or directly rotatably connected to the ceiling via the third point of articulation. In other words, the second articulated arm can modify its relative position to the ceiling by rotating or by pivoting about the third point of articulation.

The provision of a third point of articulation on the second articulated arm means that the freedom of positioning of the CT gantry can be further increased. The first and the second articulated arms, which can each respectively be pivoted relative to the gantry or the ceiling, maximally decouple the movement of the gantry from the ceiling. In particular, this decoupling enables rotation of the gantry about a vertical axis which runs through the isocenter of the gantry.

In a further preferred embodiment, the second deflection roller, about which the supply line runs in a circumferentially repositionably guided manner, is arranged in the third point of articulation. In other words, in this embodiment the second deflection roller ensures optimum deflection of the supply line between the first and second articulated arms for a plurality of relative positions between the second articulated arm and the ceiling or a previously defined ceiling axis, i.e. for a plurality of angular positions between the second articulated arm and the ceiling axis. This also applies here without a reserve loop in the third point of articulation being necessary.

In relation to the first and/or the second deflection rollers, circumferentially repositionable guidance means on the one hand that the supply line can be repositioned along its longitudinal axis relative to the deflection roller. However, circumferentially repositionable guidance also addresses the circumferential path around the respective deflection roller, the length of which may vary as a function of the relative position of the first and second articulated arms or the second articulated arm and the third point of articulation. For example, the greater the angle between the first and second points of articulation, the smaller is the circumferential path along which the supply line rests against the first deflection roller.

According to embodiments of the present invention, optimum deflection in particular means that the first and/or the second deflection roller(s) is/are designed or dimensioned such that, for a plurality of positions of the articulated arms relative to one another or to the gantry or to the ceiling-suspended third point of articulation, the length of the supply line between the connection point on the vertical column and the third point of articulation is always the same. The plurality of positions of the cable guidance system in particular comprise any positions which can be adopted on pure translation of the gantry between two maximally distant repositioning locations of the gantry. This means that, according to embodiments of the present invention, in the case of pure translation of the gantry, the requisite reserve length of the supply line is kept in hand or equalized solely by the variable repositioning paths provided circumferentially on the deflection rollers. In other words, in the event of purely longitudinal travel of the gantry, the length of the supply line between the first and third points of articulation is constant. The variable repositioning paths at the first, second and third points of articulation offset one another for each position of the gantry, providing this only moves translationally.

In some embodiments of the present invention, a further reserve of supply line is provided for rotation of the gantry, in particular about 180°, as is described in greater detail below.

In one embodiment of the present invention, the at least one supply line is guided in an energy chain, with the supply line here particularly preferably being provided over the entire length of the supply line. In the event of a relative repositioning movement of the supply line relative to further components of the cable guidance system, the energy chain is moved together with the supply line along the longitudinal axis thereof. The energy chain provides mechanical protection for the at least one supply line. In particular at the points of articulation, the at least one supply line extends at least in part without further external protection, such that it is in particular there that the energy chain prevents damage to the supply line. In addition, the outside of the supply line may be optimized with regard to its sliding behavior over its entire length in order to facilitate relative motion between the energy chain and further components of the cable guidance system. In some embodiments of the present invention, the surface may accordingly be of particularly low-friction construction. The energy chain also prevents excessive bending or kinking of the supply line which results in damage.

The second point of articulation of the cable guidance system according to embodiments of the present invention is preferably configured such that it permits positions in which the first articulated arm and the second articulated arm form an angle of between 10° and 170°. The stated angle here relates to the two longitudinal axes of the articulated arms. In other words, the second point of articulation permits orientations of the first and second articulated arms in which these are arranged almost or substantially parallel either one behind the other or adjacent one another. The first orientation enables an advantageously large distance between the vertical column and the ceiling-suspended third point of articulation, so increasing the freedom of movement for the gantry. The second-stated orientation, on the other hand, ensures a minimum footprint for the entire CT system. In other words, with this orientation of the two articulated arms, the CT system has the smallest possible base area or space requirements. This advantageously enables smaller parking spaces for the CT system when it is out of service.

In a preferred embodiment of the cable guidance system, the axis of rotation of the first deflection roller runs through the second point of articulation and the first and second articulated arms are connected together on the axis of rotation of the first deflection roller. In this way, the diameter of the first deflection roller substantially defines a minimum distance between the two articulated arms. This minimum distance is bridged by way of lever arms provided on both the first and the second articulated arms, which lever arms, at the end oriented toward the first point of articulation, extend away from the articulated arm for example at an angle of approx. 30° to 120° relative to the longitudinal axis of the articulated arm. Each articulated arm particularly preferably comprises two lever arms at the end oriented toward the first point of articulation, the free ends of the lever arms each being provided with a corresponding opening and being mounted on the axis of rotation of the first deflection roller for example by way of a pin passing through the openings. The lever arms here preferably grip the first deflection roller from both above and below. Other design variants for connecting the first and second articulated arms are likewise conceivable for the purposes of embodiments of the present invention. In some embodiments, the lever arms can increase the effective length of an articulated arm.

In a further embodiment of the cable guidance system according to the present invention, the first point of articulation is configured such that it permits positions in which the first articulated arm and the gantry form an angle of between 10° and 180°. The stated angle here relates to the longitudinal axis of the first articulated arm and a transverse axis which is to be defined beforehand of the gantry or the vertical column.

By way of the particularly broadly specified ranges of angular rotation of the first and second points of articulation, the cable guidance system in particular permits rotation of the gantry about 180° and beyond.

In a further preferred embodiment of the cable guidance system, the center axis of the cylinder segment runs through the first point of articulation and the first articulated arm is connected to the vertical column in or on the center axis.

In this manner, the radius of the cylinder segment substantially defines a minimum distance between the longitudinal axis of the first articulated arm and the transverse axis of the vertical column. This minimum distance is bridged by way of at least one and preferably two lever arms provided on the first articulated arm, which lever arms, at the end oriented toward the vertical column, likewise extend away from the first articulated arm at an angle of approx. 30° to 120° relative to the longitudinal axis of the articulated arm. Here too, the first articulated arm preferably also comprises two lever arms, the free ends of the lever arms again each being configured with a corresponding opening and being mounted on the center axis of the cylinder segment for example by way of a pin passing through the openings. Again, the lever arms preferably grip the cylinder segment from both above and below. For the sake of completeness, it should be noted that the cylinder segment is mounted fixedly on the vertical column, i.e. is not configured to rotate about its center axis. In some embodiments, the lever arms can here too increase the effective length of the first articulated arm.

In a further embodiment of the cable guidance system, the third point of articulation is configured such that it permits positions in which the second articulated arm and an axis on the ceiling which is to be defined beforehand, in particular an axis parallel to a translational repositioning direction of the gantry, for example to the longitudinal axis of the horizontal column which is described in greater detail below and along which a carriage moves, form an angle of between 10° and 270°. In this way, the freedom of movement of the CT system is further increased since the second articulated arm can thus also span a wide angular range starting from the third point of articulation. In particular embodiments, the particularly broadly defined angular range of the third point of articulation means that either the articulated arm lengths and/or the translational repositioning path provided by the horizontal column described below may be designed to be shorter without having to limit the movement radius for the gantry in particular with regard to the isocentric rotation thereof. In this way, the cable guidance system can be particularly well adapted to smaller examination environments while saving materials.

In some embodiments of the cable guidance system, the first and second articulated arms lie or move in one plane. In other words, the first, second and also third points of articulation each enable rotation or pivoting about axes of rotation arranged parallel to one another. According to a preferred variant embodiment, the two articulated arms lie in a horizontal plane and are thus arranged parallel to a subfloor or the ceiling. The points of articulation may accordingly be of particularly simple construction since, as already explained above, each one need provide just one degree of freedom of movement for the pivoting movement.

The vertical column may, however, also be configured as height-adjustable. In some embodiments, the first, second and/or third points of articulation may then be configured also to permit a pivoting movement about a horizontal axis. In this case, the height of the vertical column can readily be adapted, in particular subsequently, thus after installation of the CT system, for example in order to satisfy the spatial requirements of a specific examination or treatment environment. In other embodiments, the height of the vertical column is already set prior to installation, for example in line with a prevailing room height. It is then sufficient for the first, second and/or third points of articulation each to have just one degree of freedom. The height adjustability of the vertical column may for example be provided via a telescopic embodiment. The vertical column here comprises for example two or more hollow profile segments, pairs of which are mounted guided at least in part in one another. The vertical column may consequently be elongated by advancing the individual hollow profile segments from the respective carrying segment. Shortening may correspondingly conversely be achieved by retracting the profile segments into one another.

The height adjustability of the vertical column primarily serves to adapt the cable guidance system to existing spatial requirements, in particular a ceiling height, i.e., to equalize the height of the third point of articulation with the height of the vertical column.

The lengths of the first and second articulated arms are selected, according to embodiments of the present invention, such that the length of the first articulated arm corresponds to 65% to 75%, in particular 68% to 72%, particularly preferably 70% of the length of the second articulated arm. The inventors were able to establish empirically that this length ratio of the articulated arms particularly effectively supports freedom of movement of the gantry. In particular, this length ratio of the articulated arms supports a purely rotational movement of the gantry 180° about a vertical axis through its isocenter.

In one particularly preferred embodiment, the first articulated arm is at most 1600 mm long and the second articulated arm at most 2300 mm long. Using the stated maximum lengths of the articulated arms, a maximum travel distance for the gantry of 5600 mm can already be achieved with the previously described cable guidance system. In some embodiments, the lengths of the two articulated arms may also be shortened in accordance with the above ratio in order to adapt the cable guidance system to structural circumstances of the examination or treatment environment or the dimensions of the CT system.

In one preferred embodiment, the cable guidance system furthermore comprises a ceiling-mounted horizontal column extending above the gantry, the longitudinal axis of which column extends parallel to the translational direction of movement of the gantry. A carriage which is repositionable in the longitudinal direction of the horizontal column and bears the third point of articulation is here arranged on the horizontal column. In this embodiment, the third point of articulation, which in other embodiments may be fixedly positioned on the ceiling, may be repositioned parallel to the direction of movement of the gantry. Advantageously, the carriage may here be repositioned over substantially the entire length of the likewise ceiling-mounted horizontal column. In this way, taking the maximum lengths of the first and second articulated arms together, the maximum travel distance of the gantry can be extended to 12 m, so enabling convenient use of the computed tomography system in a plurality of treatment rooms.

Alternatively or additionally to a height-adjustable vertical column as already described above, the carriage may also be configured to adjust the height of the third point of articulation, such that the cable guidance system can also be adapted to a predetermined ceiling height by way of the carriage.

Starting from the third point of articulation on the carriage, the at least one supply line is then at least in part guided onward in at least one energy chain in the horizontal column. As has already been described above, the energy chain provides mechanical protection for the at least one supply line and in particular prevents kinking of the supply line when the carriage is repositioned between a first end of the horizontal column and the second end of the horizontal column along the longitudinal axis thereof.

In some embodiments of the present invention, the carriage can be jointly passively moved by a drive provided in the gantry or in the base of the gantry. In other embodiments, the carriage may alternatively or additionally have its own drive unit for moving the carriage actively along the horizontal column. This is in particular advantageous for transferring the CT system into its parking place or parked position in which the first and second articulated arms adopt an angle of 10° to one another, lying substantially next to one another.

In some embodiments of the present invention, the horizontal column has a length of at most 7 m along the direction of movement of the gantry. In other words, in the event of a movement of the gantry, the carriage is repositioned with the gantry over a distance of at most 7 m.

In further embodiments of the cable guidance system, the axis of rotation of the second deflection roller runs through the third point of articulation and the second articulated arm is connected to the carriage on the axis of rotation of the second deflection roller. In this way, the radius of the second deflection roller also substantially defines a minimum distance of the second articulated arm and the carriage. This minimum distance is bridged by way of lever arms provided at least on the second articulated arm, which lever arms, at the end oriented toward the third point of articulation, extend away from the articulated arm for example at an angle of approx. 30° to 120° relative to the longitudinal axis of the articulated arm. The second articulated arm particularly preferably comprises two lever arms at the end oriented toward the third point of articulation, the free ends of the lever arms again each being furnished with a corresponding opening and being mounted on the axis of rotation of the second deflection roller for example by way of a pin passing through the openings. The lever arms here preferably grip the second deflection roller from both above and below. In some embodiments, the lever arms can increase the effective length of the second articulated arm.

The above-introduced carriage of a cable guidance system, according to embodiments of the present invention, particularly preferably comprises a reserve module for providing a reserve of supply line. This reserve of supply line is required as soon as the gantry rotates isocentrically. While the reserve of supply line provided via the cylinder segment and the first and second deflection rollers is in particular sufficient to completely follow a movement of the gantry along the entire horizontal column, the reserve of supply line provided in the carriage provides an additional length of supply line such that the gantry can additionally be isocentrically rotated 180° about its own axis at any desired position along the horizontal column.

The reserve of supply line is particularly favorably arranged in or close by the carriage such that there is no loop of line hanging freely in space here either, whereby the operational reliability of the modality can be increased and the footprint advantageously kept small.

In one embodiment of the present invention, the reserve module here comprises a loop of supply line and a third deflection roller, about which the loop of supply line is circumferentially repositionably guided, arranged against a spring force. The third deflection roller is thus repositionably arranged or mounted against the spring force. The end of the reserve of supply line is for example fixed to a load-bearing component of the carriage or the housing thereof. If the reserve of supply line is required for example for rotation of the gantry, the supply line exerts tension along its longitudinal axis on the reserve module. By way of this tensile force, the third deflection roller is repositioned in the direction of the tensile force against the spring force, so at least partially releasing the reserve of supply line. If the reserve of supply line is no longer required or the tension on the reserve module declines, the spring force automatically moves the third deflection roller back into its starting position and the reserve of supply line is drawn back into or close by the carriage.

The reserve module is preferably designed such that it provides a reserve of supply line of between 45 cm and 110 cm, preferably between 55 cm and 65 cm, and particularly preferably of between 61 cm and 62 cm. The path to be equalized is here obtained as the product of the angle of rotation of the gantry (at most 180°), pi and the radius of curvature normalized to 180° (=radius of the third deflection roller).

In the above preferred embodiment, the reserve of supply line is guided around the third deflection roller according to the pulley principle. This means that the repositioning path of the third deflection roller needs to be made approximately half as long as the reserve of supply line. The repositioning path of the third deflection roller advantageously amounts to distances of between 22.5 cm and 40 cm, and particularly preferably to distances of between 28 cm and 33 cm.

The deflection rollers of the cable guidance system, according to embodiments of the present invention, are preferably all of the same dimensions. The radius of the deflection rollers preferably amounts to a value of between 18 cm and 38 cm, with smaller radii being more favorable with regard to the material costs, total weight and footprint of the system. The height of the deflection rollers here preferably amounts to approximately 20 cm. The deflection rollers preferably take the form of plastics parts (e.g. injection moldings), a central connecting piece along the axis of rotation of a deflection roller holding a base and top plate at a distance corresponding to the height of the deflection roller and the circumferences of the base and top faces jointly defining the circumferential surface of the deflection roller. In this embodiment, the at least one supply line rests against these circumferences of the base and top faces.

In a preferred embodiment, the design of the cylinder segment is selected with regard to material, height and radius in accordance with the deflection rollers.

In order to considerably simplify the assembly of the cable guidance system, according to embodiments of the present invention, the first and second articulated arms preferably each take the form of a load-bearing hollow profile, wherein the at least one supply line runs in a mounting element along the longitudinal axes of the first and second articulated arms outside the hollow profile. The mounting element should be understood as a component of each articulated arm, it being possible for the mounting element likewise to be fabricated from sheet steel. The mounting element can here be jointly formed on a hollow profile in one piece for example by bending and stamping. Alternatively, the mounting element can also be separately fabricated and then connected to a hollow profile. Depending on modality and design, the at least one supply line weighs in excess of 100 kg, which can only be lifted, held, positioned and/or mounted with considerable effort by personnel. The mounting element is here preferably of gutterlike or channel-like construction, the at least one supply line at least in part being received in the mounting element and running therein. In particular, the mounting element takes the form of a self-supporting element which is constructed to hold the at least one supply line.

In a preferred embodiment, the mounting element may be closed at the side after introduction of the least one supply line by way of a cover or panel such that the supply line is protected from environmental influences or dust.

A further aspect relates to a computed tomography system for producing tomographic X-ray images. This comprises a gantry which is repositionable in a direction of movement perpendicular to the gantry and a cable guidance system, according to embodiments of the present invention, which is configured as has already been described above. The computed tomography system is designed to generate tomographic image data of a patient, or more specifically of a part of the patient's body, using X-rays. To this end, the computed tomography system comprises imaging components in its gantry in the form of at least one X-ray source and, arranged opposite thereto, at least one X-ray detector. The X-ray source is configured to generate X-rays and emit them toward the patient who is arranged in the isocenter of the gantry. The X-rays are attenuated by the distribution of tissues in the investigated or imaged region of the body and, once they have passed through the patient, impinge on the X-ray detector. The imaging components of the CT system are arranged rotatably in the gantry such that projection data can be generated from a plurality of different angular positions. The CT system further comprises a computing unit which is configured to reconstruct a preferably three-dimensional tomographic X-ray image of the region of the body from a plurality of acquired projection data.

In some embodiments, the CT system may comprise a rail system which runs in the above-described direction of movement of the gantry. The rail system may here comprise one, but also two or more rails. In a preferred embodiment, the rails are of linear construction. In some particular embodiments, the rail system extends over a length of up to 12 m. This maximum travel distance particularly advantageously extends through two examination rooms of a medical facility. At a maximum travel distance of 12 m, two spacious examination rooms can be used with just one CT system by repositioning the gantry of the CT system along the rail system. This is assisted by the above-described cable guidance system, which in some embodiments is configured to guide with it the at least one supply line over this maximum travel distance.

In one advantageous embodiment, a parking place for storing the CT system when it is out of service is provided between the two examination rooms, this position possibly being divided from the examination rooms by way for example of sliding doors. In one particularly advantageous embodiment, this parking place may be made particularly small or narrow since the two articulated arms of the cable guidance system are positionable very close and almost parallel to one another.

In a further embodiment, the horizontal column may have a roller blind cover on the longitudinal side on which the carriage is guided. The primary purpose of the roller blind cover is to close the horizontal column. The roller blind cover may for example be made of plastics. The roller blind cover may alternatively be made of metal, in which case it limits radiation leakage between the two examination rooms.

The CT system is furthermore configured to perform a rotation of the gantry by a maximum of 180° about a vertical axis running through the isocenter of the gantry during a repositioning movement along the rail system. Alternatively, the gantry may also be rotated when stationary. The cable guidance system according to embodiments of the present invention is again of assistance here. Thanks to the specific length ratio between the first and second articulated arms, the gantry can itself perform a rotation of 180° about the isocenter axis without any translational movement along the rail system.

The CT system may comprise a rotational drive or a rotary mounting which acts between the base of the CT system and gantry. In other words, the base may be rigidly oriented and fixedly connected to the rail system. The gantry, on the other hand, can be rotated relative to the base by the rotational drive.

Example advantages of embodiments of the present invention are summarized again below:

In the case of an advantageously long translational travel distance for the gantry, the cable guidance system enables use in a two-room environment. The cable guidance system here enables a 180° rotation of the gantry about the vertical axis through its isocenter. Rotation of the gantry improves gantry accessibility, such that the patient or a patient couch together with a patient, in each of the examination rooms in a two-room environment, can be introduced from outside the examination rooms into the gantry, so greatly simplifying patient positioning and thus the course of the examination.

The cable guidance system overall requires less space since according to embodiments of the present invention it is possible to dispense with reserve loops or reserve lengths for the supply line are arranged in the interior of the cable guidance system. This advantageously creates more space for other, in particular interventional imaging systems, for example a C-arm system.

The absence of reserve loops makes the cable guidance system safer because it comprises distinctly fewer danger points for causing personal injury or damaging medical equipment in the immediate surroundings of the CT system. Dispensing with reserve loops also reduces the risk of the supply line itself undergoing excessive dynamic kinking, in particular at the rear.

By way of the load-bearing mounting element, the cable guidance system provides simple accessibility to the at least one supply line. This simplifies system maintenance. In addition, the load-bearing mounting element facilitates installation of the cable guidance system.

BRIEF DESCRIPTION OF THE DRAWINGS

The above-described characteristics, features and advantages of this invention and the manner in which these are achieved will become clearer and more distinctly comprehensible from the following description of the exemplary embodiments, which are explained in greater detail in connection with the drawings. This description does not limit the present invention to these exemplary embodiments. Identical components in different figures are provided with identical reference characters. The figures are not in general to scale. In the figures.

DETAILED DESCRIPTION

Figure 1:
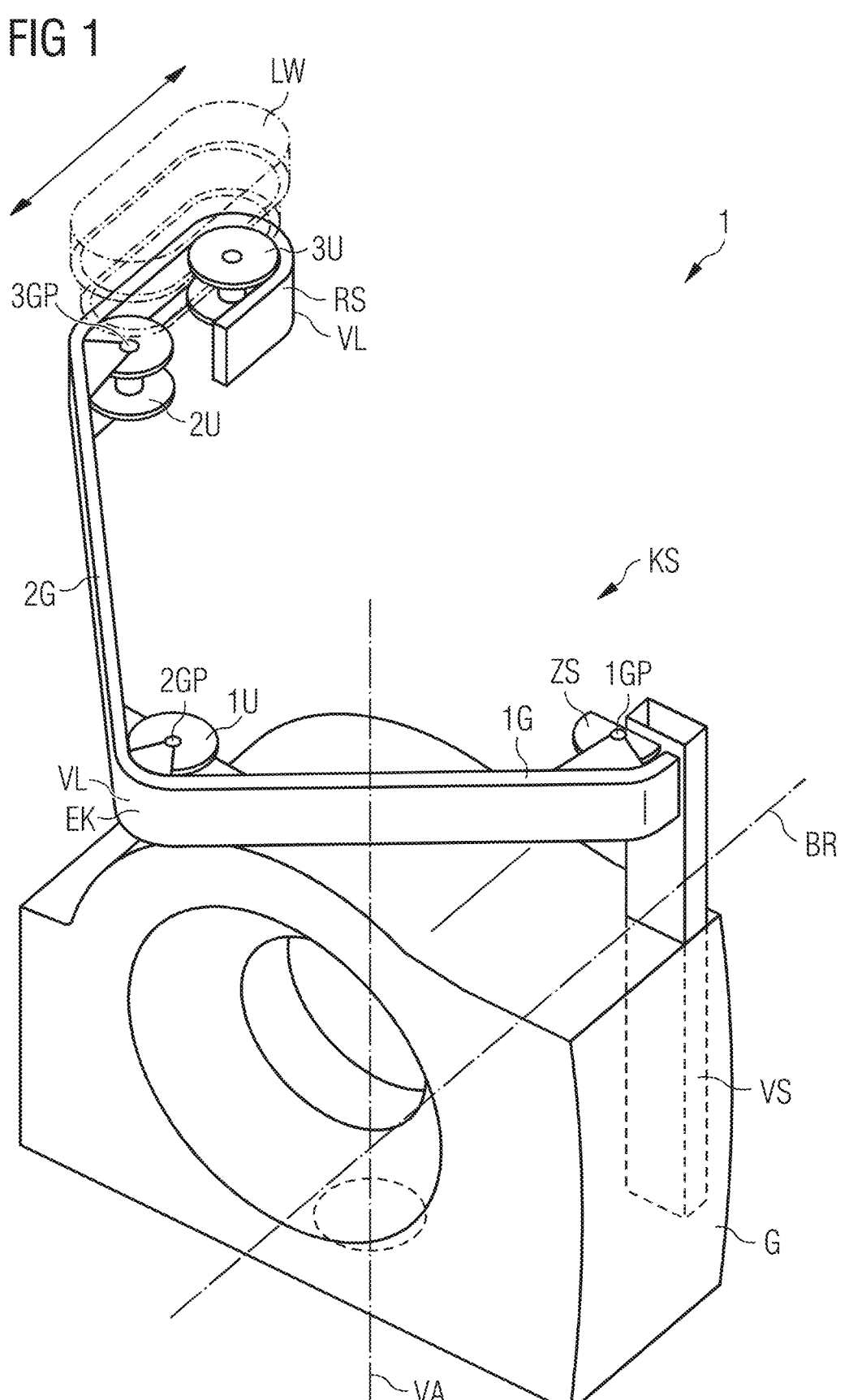
FIG. 1 shows a perspective view of a cable guidance system in a first embodiment of the present invention.

FIG. 1 shows a perspective view of a cable guidance system KS in a first embodiment of the present invention. The cable guidance system KS is configured for a computed tomography system 1. The latter has a gantry G which can be repositioned or displaced along a direction of movement BR running perpendicular to the gantry G. The cable guidance system KS here comprises a vertical column VS which is arranged at the side or corner of the gantry G and runs vertically upward from a base of the computed tomography system 1. A first articulated arm 1G and a second articulated arm 2G are furthermore included. The first articulated arm 1G is rotatably connected to an upper end of the vertical column VS above the gantry G via a first point of articulation 1GP and rotatably connected via a second point of articulation 2GP to the second articulated arm 2G which is likewise arranged above the gantry G. The first point of articulation 1GP thus allows the first articulated arm 1G to be pivoted not only above, but also at least in part across the gantry G. The second point of articulation 2GP allows a relative position between the first and second articulated arms 1G, 2G to be modified. The vertical column VS has a height which extends to above the gantry G. The height of the vertical column VS is here designed such that a minimum distance or safety margin is maintained between the highest point of the gantry G and the bottom of the first articulated arm 1G. The vertical column VS and the first and second articulated arms 1G, 2G are in each case constructed with cavities or internal regions, such that they can each guide at least one, typically a plurality of supply lines VL in the form of electrical or data cables, at least in part along their longitudinal axes. In other words, in each case subportions of the at least one supply line VL run within the vertical column VS, the first articulated arm 1G and the second articulated arm 2G. The at least one supply line VL consequently extends lengthwise at least over the total length of the vertical column VS and first and second articulated arms 1G, 2G and is guided by the course of the stated components of the cable guidance system KS.

In this embodiment, the second articulated arm 2G is rotatably connected above the gantry G via a ceiling-mounted third point of articulation 3GP. Ceiling-mounted means in this connection that the third point of articulation 3GP is mounted or fastened close to or on the ceiling. In this way, the second articulated arm 2G may also be pivoted or positioned not only above, but at least also in part across the gantry G. In this embodiment, the third point of articulation 3GP is arranged on a carriage LW. The latter is in turn mounted on a horizontal column HS which extends above the gantry G and is ceiling-mounted, i.e. attached directly to the ceiling (cf. FIG. 5). The horizontal column HS extends along its longitudinal axis parallel to the direction of movement BR of the gantry G. The carriage LW is arranged lengthwise repositionably on one longitudinal side of the horizontal column HS (cf. double-headed arrow). In this manner, the carriage LW and thus the third point of articulation 3GP can be jointly moved over substantially the entire length of the horizontal column HS in the direction of movement BR of gantry G, so advantageously increasing the freedom of movement for the gantry G. In the present case, the horizontal column HS has a length of 7 m. However, depending on the structural requirements of the medical facility, it may also be made shorter, for example 6 m, 5 m or the like. In this embodiment of the present invention, the carriage LW comprises a drive (not shown) which actively displaces the carriage LW during a repositioning movement of the gantry G. In other embodiments, the carriage may also be displaced passively or by the drive of the gantry G.

In further embodiments which are not shown here the third point of articulation 3GP is fixedly attached to the ceiling. In other words, it cannot be moved. These embodiments are particularly well adapted to single-room applications.

In the present case, the carriage LW is configured to adjust the height of the third point of articulation 3GP. In other words, the carriage permits equalization between the ceiling height and the height of the vertical column VS or the heights of the three points of articulation 1GP, 2GP, 3GP, which are always located in a common plane, preferably in a horizontal plane, thus parallel to the ceiling or subfloor. To this end, the carriage LW comprises in this embodiment a for example telescopic adjustment mechanism (not shown) in order to set the height of the third point of articulation 3GP by vertically retracting or advancing at least one telescopic segment.

In addition to the carriage LW, which can adapt the height of the third point of articulation 3GP, in the present case the vertical column VS is also configured as height-adjustable such that the height of the first and second points of articulation 1GP, 2GP may also be adapted in order to set a suitable operating plane for the points of articulation. For this purpose, in the embodiment shown at least the first and third points of articulation 1GP, 3GP are configured to permit a pivoting movement not only about a vertical axis, but also about a horizontal axis. The vertical column VS may also have a telescopic mechanism (not shown) which is preferably arranged at the upper end of the vertical column VS and sets the height of the first point of articulation 1GP by retracting and advancing at least one telescopic portion.

The at least one supply line VL continues to run at least in portions in the carriage LW, as is additionally explained below in relation to the further figures. In the present case, the at least one supply line VL is entirely guided in an energy chain EK, i.e. not only over the length of the two articulated arms 1G, 2G but also in the vertical column VS and the carriage.

The at least one supply line VL is repositionably guided along the longitudinal axes of the first and second articulated arms 1G, 2G. In other words, the relative position of the supply line VL to the articulated arms 1G, 2G is not defined, but is instead variable. At least portions of the supply line VL are thus repositionable lengthwise in the cable guidance system relative to further components of the cable guidance system KS.

To this end, in each case either a cylinder segment ZS or a first or a second deflection roller 1U, 2U, about which the at least one supply line VL is circumferentially guided, is provided in the first, second and third points of articulation 1GP, 2GP, 3GP.

In other words, the at least one supply line VL rests circumferentially at least in part against the circumferential surface of the cylinder segment ZS and the first or second deflection roller 1U, 2U. The supply line VL is here circumferentially repositionably guided. This means that the supply line VL is repositionably received along its longitudinal axis on the deflection rollers 1U, 2U. The portion of the supply line VL which runs on or around the deflection roller 1U, 2U is variable along the longitudinal axis of the supply line. In addition, as a function of a position of the cable guidance system KS, the portion of the supply line VL resting against the deflection roller 1U, 2U and the cylinder segment ZS is in each case variable in length.

Overall, the length of the supply line VL between the first point of articulation 1GP (or more precisely a connection point of the supply line VL to the vertical column VS) and the third point of articulation 3GP is precisely the length that the cable guidance system KS can, without any line reserve, adopt any desired position which is provided for purely translational movement of the gantry G of the computed tomography system 1 along the direction of movement BR. In other words, a length of supply line which is sufficient for translational movement of the gantry G is provided solely by the cylinder segment ZS and the deflection rollers 1U, 2U. Providing the gantry G moves only translationally, the length of the supply line VL between the first and third points of articulation 1GP, 3GP is thus constant.

The energy chain EK, which surrounds the supply line VL, provides additional mechanical protection for the respective portions of the supply line VL which run around the cylinder segment ZS and/or the deflection rollers 1U, 2U, since energy chains generally stabilize the at least one supply line and prevent damage or excessive kinking or twisting.

While the deflection rollers 1U, 2U are arranged rotationally in the second and third points of articulation 2GP, 3GP, the cylinder segment ZS is fixedly connected to the vertical column. The cylinder segment ZS consequently does not rotate during a repositioning movement of the gantry.

In order to permit rotation of the first deflection roller 1U and the second deflection roller 2U, the axis of rotation of the first deflection roller 1U runs in this embodiment through the second point of articulation 2GP and the first and second articulated arms 1G, 2G are connected together on the axis of rotation of the first deflection roller 1U. The axis of rotation of the second deflection roller 2U accordingly runs through the third point of articulation 3GP and the second articulated arm 2G is connected to the carriage LW on the axis of rotation of second deflection roller 2U. Relative mobility of the articulated arms 1G, 2G to one another or the carriage LW and the deflection rollers 1U, 2U is achieved in this way.

When the articulated arms 1G, 2G are pivoted, the supply line VL is repositioned or displaced relative to the longitudinal axis of the articulated arms. Since the supply line VL rests against the deflection rollers 1U, 2U, the latter are set in rotation by the supply line VL and so assist the repositioning movement and optimize deflection of the supply line VL. In the present case, the lateral outer faces of the energy chain EK are on the one hand designed for elevated static friction in order to promote rotation of the deflection rollers 1U, 2U during a repositioning movement. The lower outer face of the energy chain EK, on the other hand, is designed for low sliding friction in order to facilitate the repositioning movement relative to the articulated arms 1G, 2G.

In contrast to the deflection rollers 1U, 2U, the cylinder segment ZS is mounted rigidly on the vertical column VS. The center axis of the cylinder segment ZS here runs through the first point of articulation 1GP and the first articulated arm 1G is connected to the vertical column VS in the center axis. In this way, relative repositionability of the supply line VL relative to the vertical column VS or the gantry G is achieved.

The second point of articulation 2GP is in the present case configured such that it permits positions in which the first articulated arm and the second articulated arm 1G, 2G form an angle of between 10° and 170°. The first and third points of articulation 1GP, 3GP may consequently be almost at a maximum distance from one another (corresponding to the sum of the articulated arm lengths) or at a minimum distance from one another (corresponding to a difference between articulated arm lengths), so further increasing the freedom of movement for the gantry G.

The third point of articulation 3GP is configured such that it permits positions in which the second articulated arm 2G and the longitudinal axis of the horizontal column form an angle of between 10° and 270°. In this way, the freedom of movement of the CT system 1 is further increased since the second articulated arm 2G can thus also span a wide angular range starting from the third point of articulation 3GP.

The first point of articulation 1GP is further configured such that it permits positions in which the first articulated arm 1G and the gantry G form an angle of between 100 and 180°.

Due to the large angular ranges of the various points of articulation, the articulated system comprising the two articulated arms 1G, 2G and the three points of articulation 1GP, 2GP, 3GP permits any desired position of the gantry G. Provision of the carriage LW or the horizontal column HS further advantageously extends the movement radius of the gantry G. By way of the particularly broadly specified ranges of angular rotation of the first and second points of articulation 1GP, 2GP, the cable guidance system KS in particular permits rotation of the gantry G about 180° and beyond.

Figure 2:
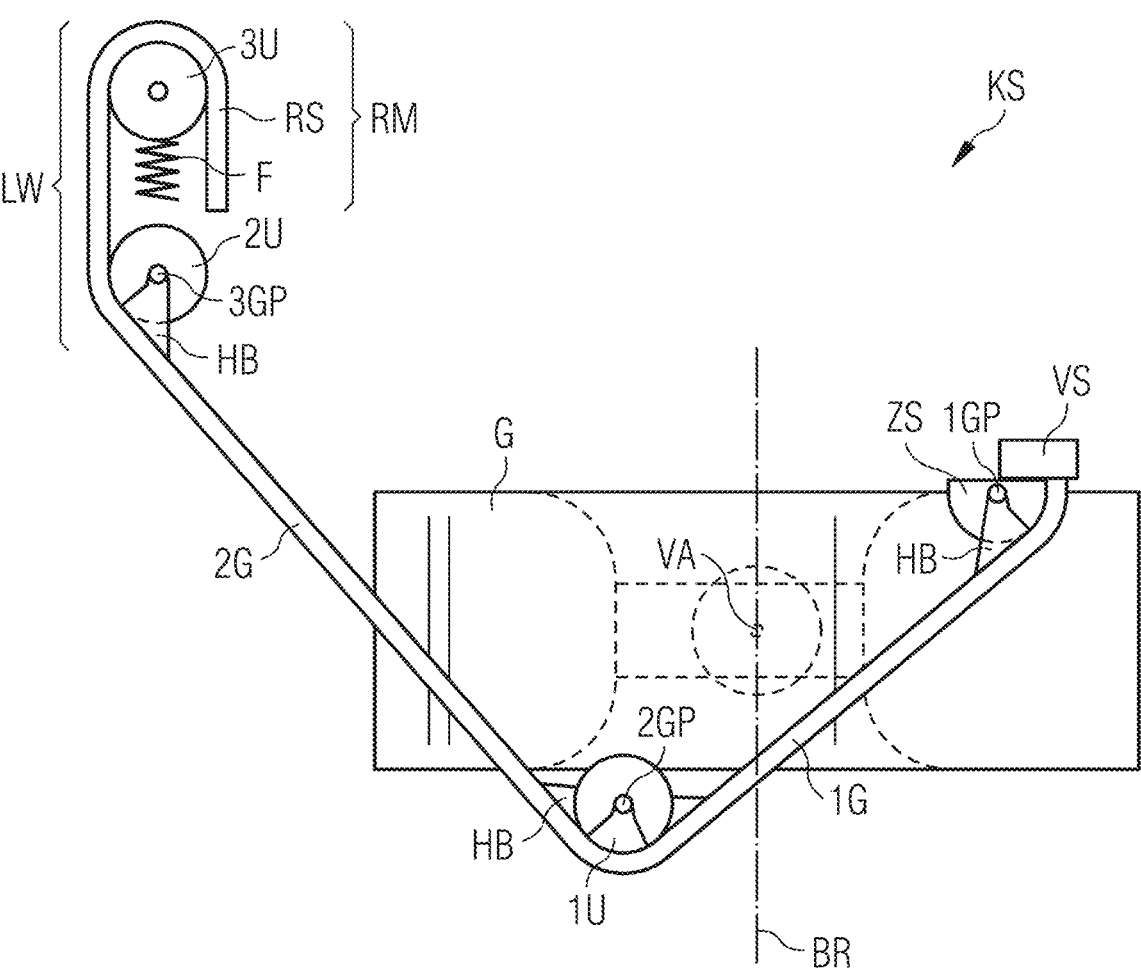
FIG. 2 shows a plan view of a cable guidance system in the embodiment according to FIG. 1.
Figure 3:
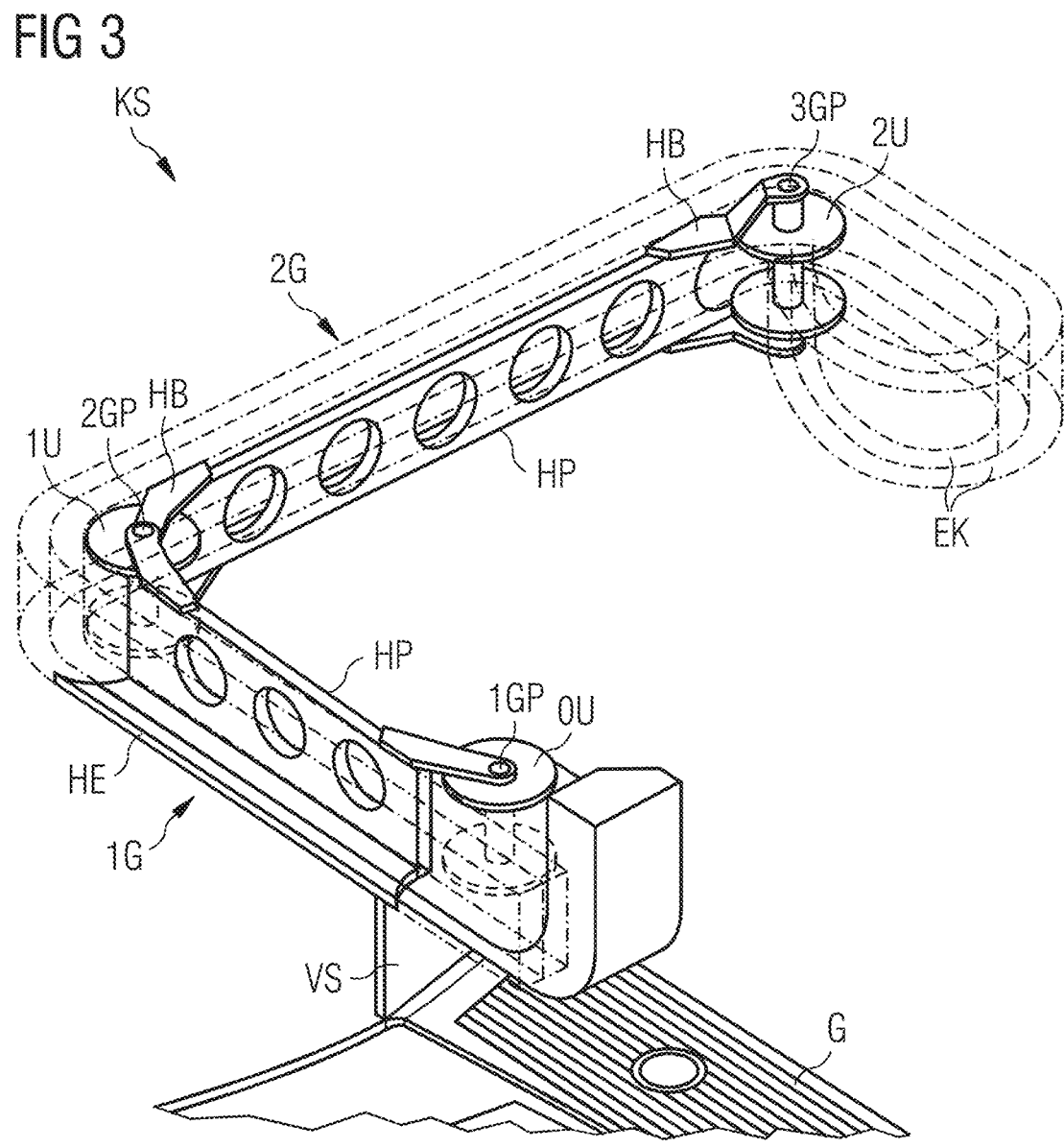
FIG. 3 shows a detail view of a cable guidance system in a further embodiment of the present invention.
Figure 4:
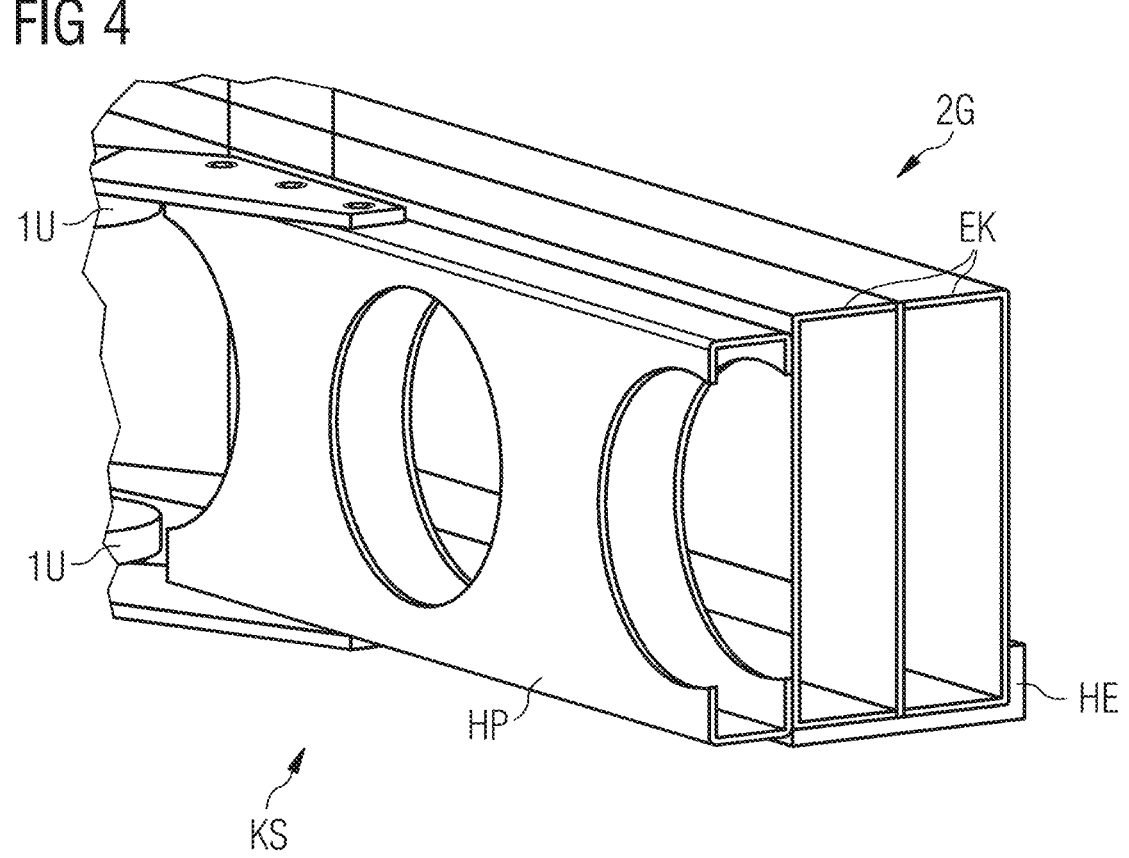
FIG. 4 shows a further detail view of the cable guidance system according to FIG. 3.

In order to achieve these large angular ranges, two lever arms HB are provided at the ends of each articulated arm 1G, 2G, which lever arms extend away from the articulated arms at an angle of between 30° and 120° and at least in part increase the effective length of an articulated arm. The lever arms HB have a length which corresponds at least to the radius of the deflection rollers 1U, 2U or of the cylinder segment ZS. The lever arms HB may be formed in one piece on the articulated arms 1G, 2G, as shown in FIGS. 1 and 2. Alternatively, the lever arms HB may also be individually fabricated and attached to the articulated arms for example by way of bolts or pins, as illustrated in FIGS. 3 and 4.

According to embodiments of the present invention, the length of the first articulated arm 1G corresponds to 65% to 75%, here approx. 70%, of the length of the second articulated arm 2G. Maintaining this length ratio allows the gantry G to be rotated when stationary by 180° about a vertical axis VA. In the present case, the dimensions of the gantry G and the use of a computed tomography system 1 in a two-room environment require the first articulated arm 1G to be 1600 mm long and the second articulated arm 2G 2300 mm long.

Without the horizontal column HS or carriage LW, the cable guidance system KS with these articulated arm lengths permits a maximum travel distance along the direction of movement BR for the gantry G of 5600 mm, while a 7 m long horizontal column HS increases the maximum travel distance to 12 m.

FIG. 2 shows a plan view of a cable guidance system in the embodiment according to FIG. 1.

As has already been explained above, the carriage LW has a reserve module RM arranged therein which provides a reserve of supply line in the form of an additional reserve loop RS in order to provide a sufficient length of the supply line for rotation of the gantry G about its vertical axis VA, in particular by 180°. In this embodiment, the reserve module RM comprises a third deflection roller 3U, about which the reserve loop RS runs in a circumferentially repositionably guided manner. Circumferentially repositionable guidance should here be taken to mean the circumferential guidance as has already been described above in relation to the first and second deflection rollers 1U, 2U. While the end of the reserve loop RS is connected to a fixed point in the carriage LW, the third deflection roller 3U is repositionably mounted against the spring force of a spring F. On rotation of the gantry G about its vertical axis VA, the supply line VL exerts a tensile force on the reserve module RM, the third deflection roller 3U being repositioned against the spring force in the direction of the tensile force, whereby the reserve loop is at least in part released or displaced into the region of the second articulated arm 2G.

FIG. 3 shows a detail view of a cable guidance system KS in a further embodiment of the present invention. In addition to the different configuration of the lever arms HB in comparison with the embodiment of the cable guidance system KS shown in FIGS. 1 and 2, a further deflecting element 0U is here provided instead of a cylinder segment ZS in the first point of articulation 1GP, via which deflecting element the supply line VL runs in a repositionably guided manner between its connection point to the vertical column VS and the first articulated arm 1G. In the present case, the first and second articulated arms 1G, 2G take the form of sheet steel hollow profile parts HP which have a substantially rectangular cross-section. The sides of the hollow profile are in the present case provided with a plurality of circular cutouts in order positively to reduce the weight of the articulated arms 1G, 2G.

FIG. 4 shows a further detail view of the cable guidance system KS according to FIG. 3. Both figures reveal the course of a gutter-shaped mounting element HE, in particular in relation to the second articulated arm 2G but which extends over substantially the entire length of each articulated arm on one of the outer sides of the hollow profile HP. Like the lever arms HB, in this embodiment the retaining elements HE are also subsequently attached to the hollow profile HP of each articulated arm 1G, 2G. Other configurations are, of course, conceivable. The mounting element HE likewise takes the form of a sheet steel component and is configured as a load-bearing structure. This makes it possible during installation or during maintenance of the cable guidance system KS to lay the at least one energy chain EK in each case together with at least one supply line VL in the mounting element HE. There is thus no longer any need for installation personnel to hold the energy chain EK in position for an extended period, but it is instead positioned there on a single occasion and then held in the mounting element HE.

The mounting element HE can then be substantially completely enclosed on the outside by way of a non-load-bearing and removable cover in order to protect the energy chain EK in the interior of the articulated arms 1G, 2G.

Figure 5:
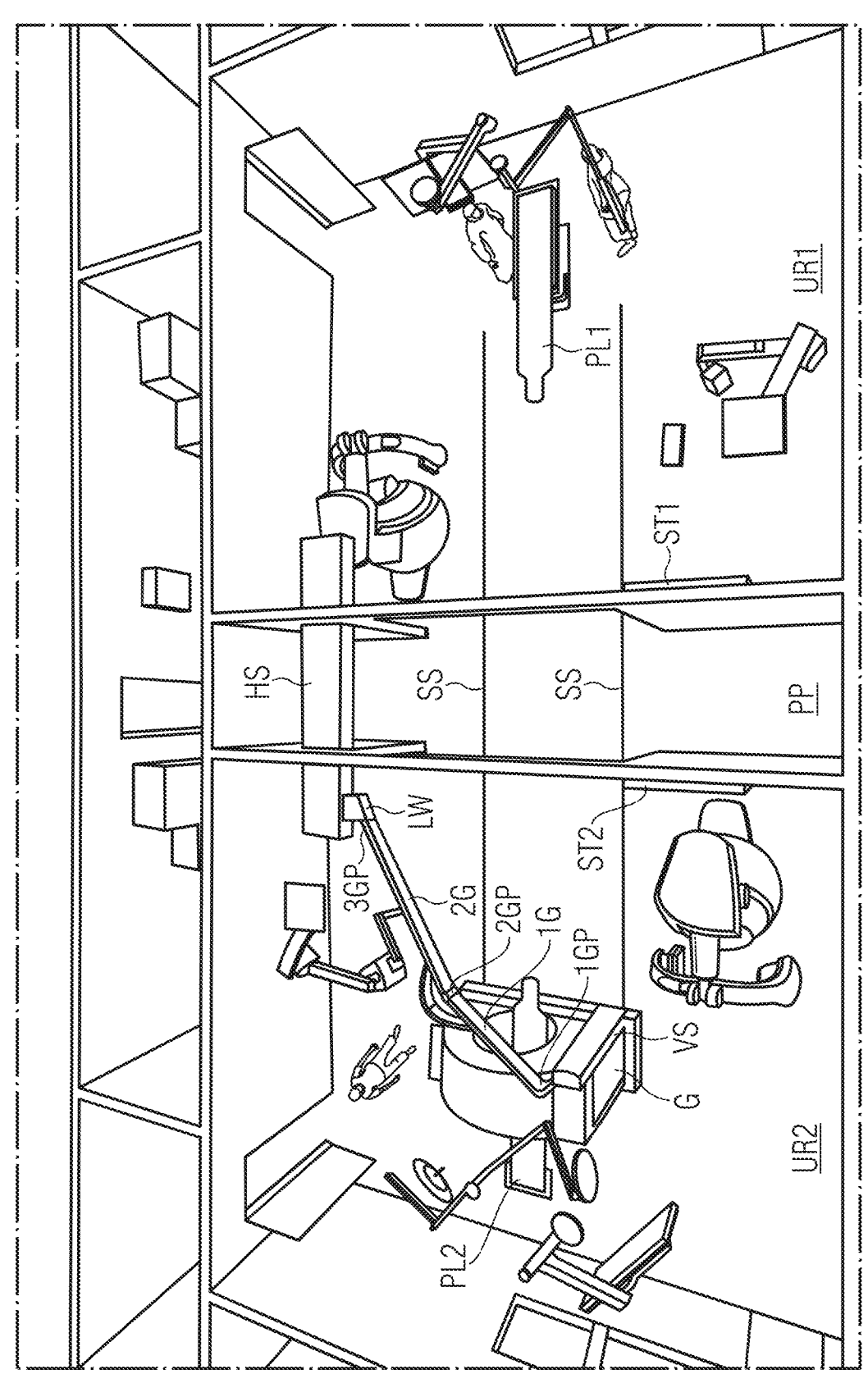
FIG. 5 shows a perspective view of a computed tomography system together with cable guidance system arranged in an examination environment in one embodiment of the present invention in an exemplary operating position.

FIGS. 4 and 5 likewise show that two upright oriented energy chains EK can be arranged and guided parallel to one another in the mounting elements HE.

FIG. 5 shows a perspective view of a computed tomography (CT) system 1 together with cable guidance system KS arranged in an examination environment in one embodiment of the present invention in an exemplary operating position. The examination environment is a two-room environment comprising two examination rooms UR1 and UR2. These are spatially separated from one another by a parking place PP for the CT system 1. If the CT system 1 is not being used or is out of service, it can be transferred into the parking place PP and the examination rooms UR1, UR2 can be put to other medical uses. To this end, further medical equipment and systems, including C arms or monitors for in situ image display or equipment for monitoring physiological functions of a patient are provided in each of the examination rooms UR1, UR2. Each examination room UR1, UR2 furthermore has a patient couch PL1, PL2 arranged therein, which is in each case fixedly, i.e. stationarily, connected to the floor. The couch tops are repositionable, in particular translationally, relative to a couch base, in order to enable fine positioning of the patient for imaging and/or an interventional measure.

The purpose of the computed tomography system 1 is to generate tomographic X-ray images in both the first and the second examination rooms UR1, UR2. It accordingly comprises a gantry G which is repositionable in a direction of movement BR running perpendicular to the gantry G. The direction of movement BR here extends along the rail system SS comprising two guide rails. As has already been described above, the rails have a length of 12 m. Their length and their course define the movement radius of the gantry G.

The gantry G is furthermore configured as rotatable about a vertical axis VA which runs through the isocenter of the computed tomography system 1. This is enabled by the cable guidance system KS already described above which comprises a plurality of components, which system is likewise encompassed by the CT system 1. In particular, the cable guidance system KS comprises a horizontal column HS with a length of 7 m which is arranged such that it extends beyond the parking place PP and projects into both examination rooms UR1, UR2. Rotation may here proceed when stationary, i.e. without parallel translation of the gantry G along the rail system SS or the carriage LW in a parallel direction, solely by repositioning of the articulated arms 1G, 2G. Rotation may alternatively proceed together with or continuously parallel to a translational movement of the gantry G along the rail system SS.

In FIG. 5, the gantry G is located in the examination room UR2 in the left-most position corresponding to the left-hand end of the rail system SS. The gantry G is rotated such that it is directed with its front side toward the outside (left) of examination room 2. In this position, patient couch PL2 projects with its top into the bore of the gantry G. Tomographic X-ray images of a patient can be generated in this position of the gantry. In order to reach this position, the cable guidance system KS adopts a maximally extended position. Point of articulation 2GP is widened to approx. 170° such that the first and second articulated arms 1G, 2G are located substantially one behind the other and their lengths are added together. Neither articulated arm 1G, 2G runs across the gantry G. The carriage LW is likewise in its left-most position in relation to the horizontal column HS. The third and first points of articulation 1GP, 3GP are nevertheless at a maximum distance from one another. In this way, the necessary length of the supply line up to a connection point at the lower end of the vertical column VS can be provided via the cable guidance system KS.

Thanks to the configuration of the cable guidance system KS, the CT system 1 is now configured to pass from the left-most position to the right-most position in the opposite examination room UR1, it being possible for various intermediate positions, in particular a position in the parking place PP, to be occupied. In the right-most position, the gantry G is rotated 180°, i.e. fully, compared to FIG. 5 and is directed with its front side toward the outside (right) of examination room UR1. In this position, patient couch PL1 projects with its top into the bore of the gantry G. Tomographic X-ray images of a patient can again be generated in this position of the gantry G. The rotation in particular means that the patient couch can be introduced into the bore in each examination room from the outside of the room and thus troublesome repositioning movements with the patient couch can be avoided, so promoting patient wellbeing and simplifying the examination procedure. In addition, patient couches PL1, PL2 can be fixedly installed in examination rooms UR1, UR2. In order to reach the right-most position, the cable guidance system KS adopts an extended, albeit not maximally extended position. Point of articulation 2GP is widened to approx. 105° such that the lengths of the first and second articulated arms 1G, 2G are largely added together. Again, neither articulated arm 1G, 2G runs across the gantry G. The carriage LW is in its right-most position in relation to the horizontal column HS. The third and first points of articulation 1GP, 3GP are at a very large distance from one another, though not at a maximum. Also in this position of the gantry G, the cable guidance system KS can provide the necessary length of the supply line up to the connection point at the lower end of the vertical column VS.

On its way from the left-most position to the right-most position, the CT system 1 can also pass through a parked position (not shown) in which the CT system 1 is out of service. The CT system 1 adopts the parked position within the parking place PP. Sliding doors ST1, ST2 of the parking place PP which were opened during the repositioning movement of the gantry G may here be closed such that each examination room UR1, UR2 can mutually independently be put to another use.

In the parked position, the gantry G adopts a previously defined, right-most position in the parking place P, it being rotated in accordance with the right-most position such that its front is oriented toward the outside (right) of examination room UR1. The second point of articulation GP2 here forms an angle of 10° between the two articulated arms 1G, 2G such that they are compactly arranged substantially adjacent one another. In particular, in this position, the second articu- lated arm 2G runs substantially parallel to the back face of the gantry. In order to reach this parked position, the carriage LW is actively moved by way of its drive to the correspond- ing position along its repositioning path on the horizontal column HS so as to achieve an angle of 10° in the second point of articulation 2GP.

Where it has not yet explicitly taken place but is reason- able and in line with the purposes of the present invention, individual exemplary embodiments, individual sub-aspects or features thereof can be combined with one another or swapped without going beyond the scope of the present invention. Advantages of the present invention described in relation to one exemplary embodiment also apply, where transferable, to other exemplary embodiments without being explicitly stated to do so.

The drawings are to be regarded as being schematic representations and elements illustrated in the drawings are not necessarily shown to scale. Rather, the various elements are represented such that their function and general purpose become apparent to a person skilled in the art. Any connec- tion or coupling between functional blocks, devices, com- ponents, or other physical or functional units shown in the drawings or described herein may also be implemented by an indirect connection or coupling. A coupling between components may also be established over a wireless con- nection. Functional blocks may be implemented in hard- ware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "inter- faced," and "coupled." Unless explicitly described as being "direct," when a relationship between first and second elements is described in the disclosure, that relationship encompasses a direct relationship where no other interven- ing elements are present between the first and second elements, and also an indirect relationship where one or more intervening elements are present (either spatially or functionally) between the first and second elements. In contrast, when an element is referred to as being "directly" connected, engaged, interfaced, or coupled to another ele- ment, there are no intervening elements present. Other words used to describe the relationship between elements should be interpreted in a like fashion (e.g., "between," versus "directly between," "adjacent," versus "directly adja- cent," etc.).

The terminology used herein is for the purpose of describ- ing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative imple- mentations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A cable guidance system for a computed tomography system, a gantry of the computed tomography system being configured to be repositioned in a first direction of movement, and the cable guidance system comprising:
   a vertical column on the gantry, the vertical column extending vertically upward from a base of the computed tomography system; and
   a first articulated arm and a second articulated arm, the first articulated arm being rotatably connected to an upper end of the vertical column via a first point of articulation, the first articulated arm being rotatably connected to the second articulated arm via a second point of articulation, the upper end of the vertical column and the second articulated arm being above the gantry, at least one supply line extending in a repositionably guided manner along longitudinal axes of the first articulated arm and the second articulated arm, at least one of the first articulated arm or the second articulated arm includes at least one of a first deflection roller or a second deflection roller, and the at least one supply line running in a circumferentially repositionably guided manner about the at least one of the first deflection roller or the second deflection roller.

2. The cable guidance system as claimed in claim 1, further comprising:
   a cylinder segment in the first point of articulation, the at least one supply line running in a circumferentially repositionably guided manner about the cylinder segment.

3. The cable guidance system as claimed in claim 2, wherein the at least one of the first deflection roller or the second deflection roller includes the first deflection roller at the second point of articulation.

4. The cable guidance system as claimed in claim 2, wherein
   the second articulated arm is rotatably connected to a ceiling-mounted third point of articulation above the gantry;
   the at least one of the first deflection roller or the second deflection roller includes the second deflection roller at the ceiling-mounted third point of articulation; and
   the at least one supply line runs in a circumferentially repositionably guided manner about the ceiling-mounted third point of articulation.

5. The cable guidance system as claimed in claim 2, wherein the at least one supply line is in an energy chain.

6. The cable guidance system as claimed in claim 1, wherein the at least one of the first deflection roller or the second deflection roller includes the first deflection roller at the second point of articulation.

7. The cable guidance system as claimed in claim 6, wherein the at least one of the first deflection roller or the second deflection roller includes the first deflection roller at the second point of articulation.

8. The cable guidance system as claimed in claim 6, wherein
   the second articulated arm is rotatably connected to a ceiling-mounted third point of articulation above the gantry;
   the at least one of the first deflection roller or the second deflection roller includes the second deflection roller at the ceiling-mounted third point of articulation; and
   the at least one supply line runs in a circumferentially repositionably guided manner about the ceiling-mounted third point of articulation.

9. The cable guidance system as claimed in claim 1, wherein
   the second articulated arm is rotatably connected to a ceiling-mounted third point of articulation above the gantry;
   the at least one of the first deflection roller or the second deflection roller includes the second deflection roller at the ceiling-mounted third point of articulation; and
   the at least one supply line runs in a circumferentially repositionably guided manner about the ceiling-mounted third point of articulation.

10. The cable guidance system as claimed in claim 9, wherein the ceiling-mounted third point of articulation is configured to permit the second articulated arm and a carriage to form angles between 10° and 270°.

11. The cable guidance system as claimed in claim 10, wherein
   a center axis of a cylinder segment runs through the first point of articulation; and
   the first articulated arm is connected to the vertical column at the center axis of the cylinder segment.

12. The cable guidance system as claimed in claim 9, further comprising:
   a ceiling-mounted horizontal column extending above the gantry, a longitudinal axis of the ceiling-mounted horizontal column extending parallel to the first direction of movement a carriage being on the ceiling-mounted horizontal column, the carriage being repositionable in a longitudinal direction of the ceiling-mounted horizontal column, and a third point of articulation being on the carriage.

13. The cable guidance system as claimed in claim 1, wherein the at least one supply line is in an energy chain.

14. The cable guidance system as claimed in claim 1, wherein the second point of articulation is configured to permit the first articulated arm and the second articulated arm to form angles between 10° and 170°.

15. The cable guidance system as claimed in claim 14, wherein the at least one of the first deflection roller or the second deflection roller includes the first deflection roller;

an axis of rotation of the first deflection roller runs through the second point of articulation; and the first articulated arm and the second articulated arm are connected together at the axis of rotation of the first deflection roller.

16. The cable guidance system as claimed in claim 1, further comprising:

a ceiling-mounted horizontal column extending above the gantry, a longitudinal axis of the ceiling-mounted horizontal column extending parallel to the first direction of movement, a carriage being on the ceiling-mounted horizontal column, the carriage being repositionable in a longitudinal direction of the ceiling-mounted horizontal column, and a third point of articulation being on the carriage.

17. The cable guidance system as claimed in claim 16, wherein the at least one of the first deflection roller or the second deflection roller includes the second deflection roller;

an axis of rotation of the second deflection roller runs through the third point of articulation; and the second articulated arm is connected to the carriage at the axis of rotation of the second deflection roller.

18. The cable guidance system as claimed in claim 16, wherein the carriage includes a reserve module configured to provide a reserve supply line.

19. The cable guidance system as claimed in claim 18, wherein the reserve module includes a loop of supply line and a third deflection roller, the third deflection roller being arranged against a spring force, and the loop of supply line being circumferentially repositionably guided about the third deflection roller.

20. A cable guidance system for a computed tomography system, the cable guidance system comprising:

a first articulated arm and a second articulated arm, each of the first articulated arm and the second articulated arm having a load-bearing hollow profile, at least one supply line running in a mounting element along longitudinal axes of the first articulated arm and the second articulated arm outside the load-bearing hollow profile, at least one of the first articulated arm or the second articulated arm includes at least one of a first deflection roller or a second deflection roller, and the at least one supply line running in a circumferentially repositionably guided manner about the at least one of the first deflection roller or the second deflection roller.

21. A computed tomography system to generate tomographic X-ray images, the computed tomography system comprising:

a gantry configured to be repositioned in a first direction of movement; and the cable guidance system as claimed in claim 1.

22. The computed tomography system as claimed in claim 21, further comprising:

a rail system, the gantry being repositionable on the rail system between two examination rooms over a distance of up to 12 m.

23. The computed tomography system as claimed in claim 22, wherein the gantry is configured to rotate 180° about a vertical axis running through an isocenter of the gantry during a repositioning movement along the rail system.

*  *  *  *  *